United States Patent
Nishioka et al.

(10) Patent No.: US 6,987,201 B2
(45) Date of Patent: Jan. 17, 2006

(54) ACETIC ANHYDRIDE, METHOD OF PURIFYING CRUDE ACETIC ANHYDRIDE, AND METHOD OF PRODUCING POLYOXYTETRAMETHYLENE GLYCOL USING ACETIC ANHYDRIDE

(75) Inventors: Seiji Nishioka, Hyogo (JP); Ryosuke Maeda, Hyogo (JP); Toshifumi Fukui, Hyogo (JP); Mitsuru Yamashita, Hyogo (JP)

(73) Assignee: Daicel Chemical Industries, Ltd., (JP)

( * ) Notice: Subject to any disclaimer, the term of this patent is extended or adjusted under 35 U.S.C. 154(b) by 0 days.

(21) Appl. No.: 09/788,047

(22) Filed: Feb. 16, 2001

(65) Prior Publication Data

US 2001/0029309 A1    Oct. 11, 2001

(30) Foreign Application Priority Data

| Feb. 17, 2000 | (JP) | ............................. 2000-039180 |
| Feb. 17, 2000 | (JP) | ............................. 2000-039977 |
| May 18, 2000 | (JP) | ............................. 2000-146694 |

(51) Int. Cl.
- *C07C 51/573* (2006.01)
- *C07C 41/01* (2006.01)
- *C07C 41/34* (2006.01)
- *C07C 41/42* (2006.01)
- *C07C 43/04* (2006.01)

(52) U.S. Cl. .................. 562/898; 203/31; 528/405; 528/408; 528/417; 528/501; 562/887; 568/617; 568/621

(58) Field of Classification Search ............... 203/31; 528/405, 408, 417, 501; 562/887, 898; 568/617, 568/621

See application file for complete search history.

(56) References Cited

U.S. PATENT DOCUMENTS

| 4,189,566 | A | * | 2/1980 | Mueller et al. | .............. 528/408 |
| 4,243,799 | A | * | 1/1981 | Mueller et al. | .............. 528/409 |
| 4,259,531 | A | * | 3/1981 | Huchler et al. | .............. 568/617 |
| 4,803,299 | A | * | 2/1989 | Mueller | ...................... 560/240 |
| 5,362,365 | A | * | 11/1994 | Niijima et al. | ................. 203/31 |
| 5,463,020 | A | * | 10/1995 | Becker et al. | .............. 528/408 |
| 5,648,558 | A | * | 7/1997 | Hatano et al. | .............. 568/618 |
| 6,403,842 | B1 | * | 6/2002 | Kobayashi et al. | ......... 568/617 |

FOREIGN PATENT DOCUMENTS

| EP | 1020484 | * | 7/2000 |
| JP | 45-22341 | * | 7/1970 |
| JP | 60222439 | | 11/1985 |
| JP | 6025071 | | 2/1994 |
| JP | 8231706 | | 9/1996 |
| JP | 2000-204152 | | 1/2000 |

* cited by examiner

Primary Examiner—Rabon Sergent
(74) Attorney, Agent, or Firm—Barbara A. Wrigley; Oppenheimer Wolff & Donnelly LLP

(57) ABSTRACT

The present invention provides acetic anhydride, a method of purifying crude acetic anhydride, and a method of producing polyoxytetramethylene glycol using acetic anhydride.

A method of producing polyoxytetramethylene glycol by ring-opening-polymerizing tetrahydrofuran in the presence of acetic anhydride and an acid catalyst, wherein said ring-opening polymerization is conducted using acetic anhydride having a diketene concentration of 10 ppm or less to produce polyoxytetramethylene glycol.

5 Claims, 1 Drawing Sheet

ACETIC ANHYDRIDE, METHOD OF PURIFYING CRUDE ACETIC ANHYDRIDE, AND METHOD OF PRODUCING POLYOXYTETRAMETHYLENE GLYCOL USING ACETIC ANHYDRIDE

BACKGROUND OF THE INVENTION

1. Field of the Invention

The present invention relates to acetic anhydride, a method of purifying crude acetic anhydride, and a method of producing polyoxytetramethylene glycol using acetic anhydride.

2. Description of Prior Art

Acetic anhydride is widely used as a raw material of cellulose acetate, or in pharmaceuticals, agricultural chemicals (acephate, etc.), dyes, face washing agents, sweeteners (aspartame, etc.), plasticizers (tributyl citrate, etc.), polymer field (polyoxytetramethylene glycol, polyacetal, liquid crystal polymer, etc.), and the like. Particularly, polyoxytetramethylene glycol (hereinafter, abbreviated as PTMG) is an industrially useful polymer which is used as a main raw material of polyurethane, polyether ester and polyether (ester) amide used in spandex, elastomer, artificial leather and the like, or as a surfactant, pressure liquid and the like, and recently, also noticed as an engineering material, medical polymer material and the like typically in the elastomer field.

There are various methods for producing this PTMG, and usually, a method is known in which tetrahydrofuran (hereinafter, abbreviated as THF) is ring-opening-polymerized in the presence of acetic anhydride and a solid acid catalyst to produce polyoxytetramethylene glycol diester (hereinafter, abbreviated as PTMGAC), then, PTMGAC is hydrolyzed in the presence of an alkali catalyst or ester-exchanged with lower alcohol to produce PTMG (e.g., JP-A No. 4-306228).

However, conventional PTMG produced by the above-mentioned method does not necessarily have excellent evaluation results of hue which is an important index of the quality, for example, APHA value, and causes a problem that PTMG which is slightly colored tends to be produced.

SUMMARY OF THE INVENTION

The present invention has been made in view of the above-mentioned problems, and an object thereof is to provide a production method which can produce PTMG of high quality excellent in hue.

Further, an object of the present invention is to provide purified acetic anhydride which is used as a raw material of PTMG of high quality excellent in hue which causes no problem in quality such as coloring and the like by heating and the like.

The present inventors have intensively studies various factors influencing the quality of PTMG for attaining the above-mentioned objects, and resultantly, found that a diketene contained in acetic anhydride exerts significant influence on the quality of a product, leading to completion of the present invention.

Namely, a method of producing PTMG of the present invention is a method of producing PTMG by ring-opening-polymerizing THF in the presence of acetic anhydride and an acid catalyst, wherein the above-mentioned ring-opening polymerization is conducted using acetic anhydride having a diketene concentration of 10 ppm or less to produce PTMG.

In this case, if acetic anhydride containing little diketene having a diketene concentration of 2 ppm (detection limit) is used, PTMG having further excellent hue can be produced.

PTMG of the present invention is produced by ring-opening-polymerizing THF in the presence of an acid catalyst and purified acetic anhydride obtained by distilling crude acetic anhydride then treating the distilled product with an ozone-containing gas.

The purified acetic anhydride causing no problem in quality such as coloring and the like by heating and the like of the present invention (used as a raw material of PTMG of the present invention) is produced, for example, by purification by ozone treatment after distillation, further by allowing an ozonization intermediate and dissolved ozone to present in suitable amount in acetic anhydride.

DETAILED DESCRIPTION OF THE PREFERRED EMBODIMENTS

Figure 1:
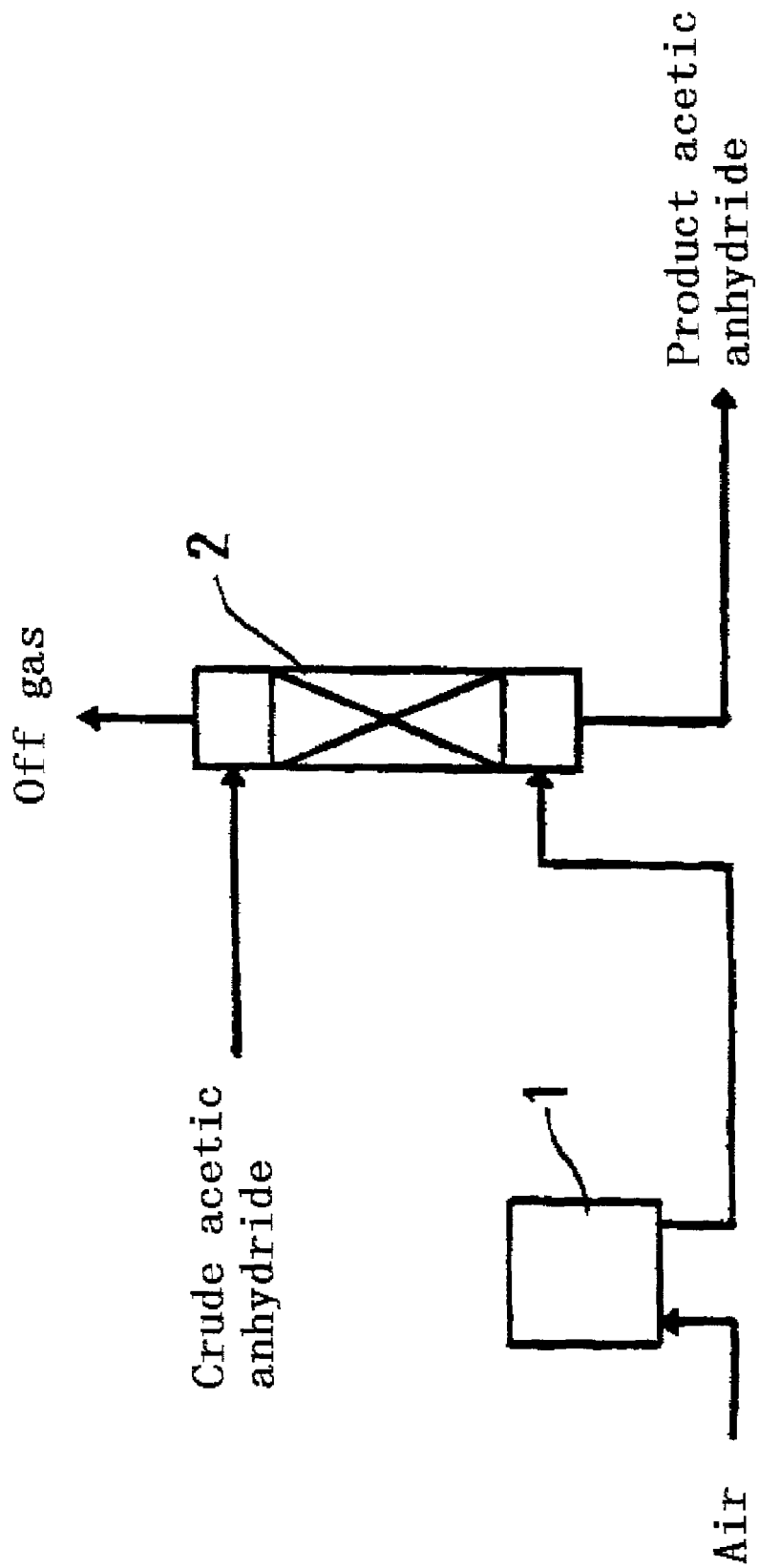
FIG. 1 is a schematic view showing the constitution of an apparatus used in conducting ozone treatment on crude acetic anhydride.

Next, embodiments of the present invention will be described in detail below. In the method of producing PTMG of the present invention, in approximately the same manner as described above, THF is ring-opening-polymerized in the presence of acetic anhydride and an acid catalyst to produce PTMGAC, then, PTMGAC is hydrolyzed in the presence of an alkali catalyst or ether-exchanged with lower alcohol, to produce PTMG.

In this case, as the acetic acid used in ring-opening-polymerizing THF, acetic acid having a diketene concentration of 10 ppm or less is used.

Such a method of producing acetic anhydride is not particularly restricted, and acetic acid obtained by effecting ozonization treatment on crude acetic acid then distilling the ozonized product can be used. By such purification treatment, crude acetic anhydride having a diketene concentration of about 5 ppm can be obtained.

The method of producing crude acetic anhydride is not particularly restricted, and for example, there are a method in which acetic acid is thermally decomposed to produce a ketene, and acetic acid is allowed to absorb and react with this ketene, to obtain acetic anhydride (ketene method), a method in which carbon monoxide is allowed to react with methyl acetate or dimethyl ether to obtain acetic anhydride, as well as other methods, and crude acetic anhydride obtained by these methods is applied.

On the other hand, if crude acetic anhydride obtained as described above is subjected to a purification process in which distillation is first conducted, then, ozone treatment is conducted, it is possible to obtain purified acetic anhydride containing little diketene having a diketene concentration of 2 ppm (detection limit) or less. The method of purifying acetic anhydride in this case will be described below.

First, the mode of a distillation column used in primary purification by distilling crude acetic anhydride is not particularly restricted, and can be selected freely. In general, it is possible to use one or more columns selected from plate columns such as a sieve tray, bubble cap tray, valve tray and the like, packed towers such as an interlocks saddle, ball ring, throughzer bag and the like.

In the case of the plate column, tray number of about 20 to 80 is preferable, and in the case of the packed column, that having the corresponding packed height is preferably used. Acetic anhydride to be purified is introduced through the intermediate part of the distillation column, and it is necessary that the introduction position is upper than the position for recovering the produce acetic anhydride, and desirably, parts upper than the center position of the distillation column are selected. The product acetic anhydride is recovered in the form of vapor or liquid from parts lower than the raw material introduction stage, desirably parts lower than the center position of the distillation column.

The operation pressure of the distillation column is not particularly restricted, and when the pressure is too high, there is a fear of occurrence of an undesirable reaction by increase in intra-column temperature, while, when the pressure is too low, condensation of vapor at the column top is followed by difficulty. Therefore, the desirable operation pressure is in the range from 100 mmHg to normal pressure at the column top.

A part of condensation liquid of the column top vapor is returned to the column top as reflux liquid, and the ratio of reflux liquid flow to the recovering liquid flow, namely reflux ratio is determined depending on the composition of the raw material liquid, required quality of the product, and the like. It can be selected usually in the range from about 0.5 to 1000, preferably from about 1 to 100.

Next, when crude acetic anhydride primary-purified using the above-described distillation column is secondary-purified by ozone treatment, the ozone-containing gas used in this procedure is also not restricted particularly. Industrially, a method is generally used in which ozone is generated by silent discharge using air or oxygen as a raw material. Usually, in the case of an air material, the ozone concentration is from 5 to 25 $g/Nm^3$, preferably from 10 to 20 $g/Nm^3$. Regarding the ratio of ozone to be contacted with acetic anhydride, it may be recommendable to charge somewhat excess amount of ozone for completely stop the reaction in view of the amount of unsaturated compounds contained in acetic anhydride primary-purified by distillation, a decomposition reaction of ozone itself, and the like. Practically, it is necessary to determine the ratio appropriately by experiments in view of the gas-liquid contact efficiency and purification efficiency, and usually, the ozone use ratio is from 50 to 300 $g-O_3/T$, preferably from 90 to 270 $g-O_3/T$.

The form of a reaction vessel for the ozone treatment is also not particularly restricted providing contact of ozone with acetic anhydride can be conducted successfully, and practically, a bubble tower mode and an agitating vessel mode are preferable. Further, as the contact time, suitable time in the range from decades seconds to dozens minutes may advantageously be set. The reaction temperature is suitably near room temperature, and preferably from about 20 to 30° C. When the temperature is too low, the reaction speed decreases, while when too high, ozone itself is not decomposed easily, undesirably.

By such a purification method, crude acetic anhydride having a diketene concentration of 2 ppm (detection limit) or less can be obtained.

On the other hand, the above-mentioned acid catalyst used in ring-opening-polymerizing THF is also not restricted particularly, and those public-known can be used. For example, solid acid catalysts such as super strong acidic cation exchange resin, bleached soil, zeolite and the like are listed. Liquid acids such as perchloric acid can also be used, however, this case is industrially disadvantageous since a process for neutralizing and/or separating an acid after the ring-opening-polymerization is complicated. Use of a solid acid catalyst is preferable, since separation of a catalyst can be conducted simply in this case. A solid acid catalyst can be used in any of a suspension bed and fixed bed, and use of the catalyst in a fixed bed flow reaction is particularly preferable since it is not necessary to separately conduct a catalyst separation operation in this case.

The reaction conditions in ring-opening-polymerizing THF vary depending on the molecular weight of the intended PTMG, ad the kind of an acid catalyst used, and usually, the concentration of an acid catalyst in the reaction liquid is from 0.1 to 50% by weight, the concentration of acetic anhydride is from about 0.1 to 30% by weight.

The reaction temperature is usually selected in the range from 0.5 to 10 hours. Since the resulted polymerization reaction liquid contains PTMGAC and unreacted raw materials and the like, usually unreacted THF and acetic anhydride are distilled off under normal pressure or reduced pressure.

By such a production method, PTMGAC is produced from THF. Then, production of PTMG from this PTMGAC is usually conducted by replacing an end ester group with a hydroxyl group by hydrolysis or alcoholysis in the presence of an alkali catalyst.

First, production of PTMG by hydrolysis in the presence of an alkali catalyst will be described. This alkali hydrolysis is a method in which an alkali aqueous solution is added in the presence of an organic solvent, and heated to substitute an end ester group with a hydroxyl group. As the organic solvent, compounds which are separated from water, such as aromatic hydrocarbons like benzene, toluene, xylene and the like, aliphatic alcohols like n-butanol and the like, aliphatic ethers like diisopropyl ether and the like are used.

As the alkali catalyst, hydroxides of alkali metals and alkaline earth metals such as sodium hydroxide, potassium hydroxide, calcium hydroxide and the like are used. These hydroxides are usually used as an aqueous solution. This aqueous solution is usually used in a concentration of 1 to 50% by weight.

The amount of this aqueous solution added differs depending on the weight of water based on PTMGAC used, and usually, the aqueous solution is so used that the weight of water based on PTMGAC is 0.1 to 10-fold, and the concentration of an alkali based on the total weight of PTMGAC, water and the alkali is from 0.01 to 40% by weight. The alkali hydrolysis temperature differs depending on the alkali concentration and the kind of an alkali used, and usually in the range from 50 to 150° C. Further, also alkali hydrolysis time differs depending on the alkali concentration, the kind of an alkali used, and the hydrolysis temperature, and usually, in the range from 0.1 to 20 hours.

The reaction crude solution containing water after completion of the alkali hydrolysis is separated into an organic layer and aqueous layer for example by a centrifugal separator, and an organic solvent and water are evaporated from the recovered organic layer by using an evaporator having a short residence time such as a thin layer evaporator, to obtain the product PTMG.

Then, production of PTMG from PTMGAC by substituting an end ester group with a hydroxyl group by alcoholysis in the presence of an alkali catalyst will be described.

The alcoholysis is a method in which PTMG is produced while extracting the by-produced carboxylate by azeotrope with alcohol by reaction distillation, using aliphatic alcohol such as methanol and the like. As this alcohol, ethanol, butanol and the like are used in addition to methanol. Among them, methanol is most preferable from the standpoints of cost, reactivity, and separation property between raw material alcohol and an ester produced by the reaction.

As the alkali catalyst, alkaline earth metal oxides, or alcoholates of alkali metals or alkaline earth metal are used. As the alkaline earth metal oxide, magnesium oxide, calcium oxide and strontium oxide are preferable. This catalyst is usually used in the form of a powder, and may also be used in the tablet form, and the form may appropriately be selected advantageously by selection of the reaction mode and catalyst separation method.

The amount of the catalyst used is usually from 0.1 to 10% by weight, more preferably from 0.5 to 3% by weight in terms of the concentration of the catalyst in the reaction crude solution. When the catalyst is a powder, the catalyst concentration may also be lower since the contact surface area per unit weight of the catalyst with reaction crude solution is large, and in the case of a catalyst which has been tabletted and molded, higher catalyst concentration is preferable wince the contact area per unit weight of the catalyst is small.

On the other hand, when an alcoholate of alkali metals or alkaline earth metals is used as the catalyst in alcoholysis, the catalyst concentration differs depending on the kind of the catalyst, and from 0.01 to 3% by weight. Further, the catalyst is used in the form of an alcohol solution from the standpoint of handling easiness.

The reaction temperature of alcoholysis is not particularly restricted, and usually from 30 to 120° C. under normal pressure. In the case of a reaction with alcohol in which the reaction temperature is over 120° C. under normal pressure, the final product gets poor hue, therefore, it is preferable, in such a case, to conduct the reaction under reduced pressure so that the reaction temperature in a vessel of a distillation column is 120° C. On the other hand, when the reaction temperature is too low, the time before completion of the reaction is too long, undesirably. Further, when alcohol having lower boiling point such as methanol, ethanol and the like is used, the reaction may also be conducted under positive pressure to increase the reaction temperature in a vessel of a distillation column and to shorten the time before completion of the reaction.

Alcoholysis may be conducted in batch-wise mode or continuous mode, and in the case of the batch-wise mode, a catalyst, PTMGAC and alcohol are charged in a vessel of a batch distillation column equipped with a reflux apparatus and reaction distillation is conducted, carboxylates produced in the vessel is distilled off by azeotrope with alcohol, then, a reaction is conducted until the column top temperature reaches the boiling point of the alcohol, to complete the alcoholysis.

In the case of the continuous mode, a catalyst, PTMGAC and alcohol are continuously charged into a continuous distillation column so as to obtain residence time to complete the reaction, the produced carboxylate is continuously extracted in the form of an azeotropic mixture with the raw material alcohol from the top of the continuous distillation column, and the unreacted alcohol, produced PTMG and catalyst are extracted continuously from the vessel. The distillation column, in this case, differs depending on the kind thereof, fillers and distillation mode (continuous distillation, batch-wise distillation), and it is preferable to use a distillation column having a theoretical stage number of 20 to 100.

When a distillation column having lower theoretical stage number is used, separation between raw material alcohol and an azeotropic mixture of the raw material alcohol with the produced carboxylate is difficult. Usually, since an azeotropic mixture of raw material alcohol with the produced carboxylate is burnt, when separation between raw material alcohol and an azeotropic mixture of the raw material alcohol with the produced carboxylate is poor, the amount of the raw material alcohol used increases, indicating undesirable phenomenon. On the other hand, when a distillation column having higher theoretical stage number is used, since more stages than necessary for separation between raw material alcohol and an azeotropic mixture of the raw material alcohol with the produced carboxylate are present, equipment cost increases and also running cost increases.

The reaction time (residence time) of alcoholysis is determined by the catalyst temperature, reaction temperature and the molar ratio of raw material alcohol to PTMGAC, and usually in the range from 1 to 10 hours. When the reaction time is too long, excess residence time is left even if the reaction is terminated, leading to reduction in the production amount of PTMG, while when the reaction time is too short, the production reaction of PTMG by alcoholysis of PTMGAC is not completed. Since an ester residue in PTMG deteriorates the quality of a product such as polyurethane and the like produced from PTMG, it is necessary that the reaction to produce PTMG from PTMGAC is completed.

The molar ratio of PTMGAC to alcohol used in alcoholysis differs also depending on the number-average molecular weight and degree of dispersion of PTMGAC, and usually the molar ratio of alcohol to PTMGAC is selected in the range from 3 to 100. When the molar ratio of alcohol to PTMGAC is too low, alcoholysis is delayed significantly and the reaction time is elongated, additionally, there is a fear of no completion of the reaction, meaning undesirable phenomenon. On the other hand, when the molar ratio of alcohol to PTMGAC is too high, energy cost required for alcoholysis increases and the amount of alcohol flushed after alcoholysis increases, leading to increase in energy cost, undesirably.

When there is a catalyst insoluble in the reaction crude solution from the bottom product of a distillation column produced by alcoholysis of PTMGAC in the presence of an alkaline earth metal oxide catalyst, the catalyst is usually separated and removed by filtration separation or centrifugal separation, and to recover and recycle unreacted alcohol, flushing is effected using a flushing apparatus having shorter residence time such as a thin layer evaporator and the like.

Crude PTMG obtained from the bottom of a thin layer evaporator contains a catalyst component dissolved in the reaction crude solution, and to remove these catalyst component and oligomer, water and crude PTMG are charged in a stirring vessel, and stirred for several hours while heating. After completion of washing while stirring, the mixture is separated by a centrifugal separator, then, separated into an aqueous layer and an organic layer and the organic layer is recovered, and the organic solvent and water are evaporated by using an evaporator having shorter residence time such as a thin layer evaporator, to obtain the product PTMG.

By using purified acetic anhydride having a diketene concentration of 10 ppm or less, preferably 2 ppm or less as the acetic anhydride used in a process to first produce PTMG by ring-opening-polymerizing THF, according to the production method as described above, PTMG having excellent hue can be obtained.

Next, acetic anhydride having a value of a sulfuric acid coloring test of 10 APHA or less after performing heat treatment at 80 to 120° C. for 5 hours or more, used in producing the above-mentioned PTMG having excellent hue is described.

As described above, as the industrial method of producing acetic anhydride, a ketene method (Wacker process) in which acetic acid is thermally decomposed to produce a ketene, and acetic acid is allowed to absorb and react with this ketene, to obtain acetic anhydride, and a halcon method in which carbon monoxide is allowed to react with methyl acetate to obtain acetic anhydride, as well as other methods are known, and the ketene method by thermal decomposition of acetic acid is conventionally general.

In the ketene method, in crude acetic anhydride obtained by allowing acetic acid to absorb and react with ketene obtained by thermal decomposition of acetic acid, impurities such as unsaturated compounds and the like are mixed in considerable amount.

Further, as the raw material acetic acid of acetic anhydride, acetic acid condensed and recovered from an acetic acid aqueous solution discharged from a process of producing cellulose acetate is used in some times, and this condensed acetic acid contains impurities not completely removed from the cellulose acetate production process, consequently, the produced crude acetic anhydride is also influenced by them.

Since the crude acetic anhydride contains impurities such as unsaturated compounds having lower boiling point and higher boiling point, and the like, components having lower boiling point and higher boiling point are usually removed by distillation.

However, purification by distillation requires a large amount of thermal energy, and, those having boiling point near that of acetic anhydride or manifesting azeotrope can not be separated sufficiently. For solving such problem of purification by distillation, JP-A No. 4-34537 discloses a purification method in which ozone treatment is performed on crude acetic anhydride obtained through a ketene furnace, namely a mixture (AA/AC≈80/20) of acetic anhydride (AA) and acetic acid (AC). By ozone treatment of crude acetic anhydride, impurities such as unsaturated compounds and the like are ozonized, and decomposed via production of an ozonization intermediate. In the ozone-treated crude acetic anhydride, in addition to presence of decomposed products obtained by ozonization of impurities such as unsaturated compounds and by decomposition via an ozonization intermediate, the ozonization intermediate before decomposition is present, also unreacted ozone is present as dissolved ozone. This acetic anhydride after the treatment can be used in the cellulose acetate production process, however, since the purity is low, acetic anhydride having further higher purity is required in some kinds of methods.

Then, JP-A No. 6-25071 discloses a method of purifying crude acetic anhydride in which ozone treatment is effected before distillation is conducted. In this method, decomposition products obtained by ozonizing impurities such as unsaturated compounds and the like, further, an ozonization intermediate, and dissolved ozone, are removed by distillation, leading to high purification.

However, it has become apparent that also in acetic anhydride purified by the method in which ozone treatment is effected before distillation conducted, impurities such as unsaturated compounds and the like are present, and problems in quality such as coloring and the like occur by heating. Also it has been become apparent that when acetic anhydride purified by the method in which ozone treatment is effected before distillation conducted is used as an agent for acetylating organic chemicals, for example, in the case of production of polytetramethylene glycol (PTMG), and the like, the final products such as PTMG and the like are slightly colored by co-use with an acid such as sulfuric acid and the like or by performing heating, causing reduction in the quality of the final product.

Acetic anhydride of the present invention is produced by purifying crude acetic anhydride not by the method in which ozone treatment is effected before distillation is conducted as described above, but by a method in which distillation is effected before ozone treatment is conducted, further, by allowing an ozonization intermediate and dissolved ozone to present in suitable amount in the acetic anhydride (coloring of acetic anhydride by heating is suppressed).

Acetic anhydride of the present invention is produced by two-stage purification treatment in which distillation is conducted before performing ozone treatment on crude acetic anhydride produced by the above-mentioned ketene method, and for example, is produced by further performing heat treatment after the above-mentioned purification treatment. By the above-mentioned production method, an ozonization intermediate and dissolved ozone can be allowed to present in crude acetic anhydride, and the amounts of the ozonization intermediate and dissolved ozone can be controlled.

The raw material crude acetic anhydride may be crude acetic anhydride having any concentration in a process of producing acetic anhydride. However, when the amount of impurities in crude acetic anhydride obtained by the reaction process is higher, the amount of consumption of an ozone-containing gas described later increases, consequently, it is desirable to produce crude acetic anhydride by selecting reaction conditions under which the amount of double bond components such as for example diketenes and the like contained in the crude acetic anhydride is lower.

The method for performing distillation before ozone treatment on crude acetic anhydride may be approximately the same as the above-mentioned method for obtaining crude acetic anhydride having a diketene concentration of 2 ppm (detection limit) or less. In this case, ozone to be contact with acetic anhydride is so charged that the amount of dissolved ozone remaining after completion of the reaction is from 10 to 100 ppm, preferably from 10 to 60 ppm, further preferably from 10 to 50 ppm. By such a purification method, acetic anhydride of the present invention which can satisfy the condition that the value of a sulfuric acid coloring test after performing heat treatment at 80 to 120° C. for 5 hours or more is 10 APHA or less, can be obtained.

The conditions of heat treatment when crude acetic anhydride which is obtained by distillation and then ozone treatment is further subjected to heat treatment may advantageously be set in the range of a temperature from 80 to 120° C. and a time from 5 to 20 hours.

Thus, by conducting primary-purification by distilling crude acetic anhydride, then, by conducting secondary-purification by treatment with an ozone-containing gas set as described above, or by purification by further performing heat treatment after the above-mentioned purification treatment, acetic anhydride of the present invention is produced.

In acetic anhydride of the present invention obtained as described above, usually, the purity is 95% or more, preferably 99% or more, dissolved ozone, and an ozonization intermediate produced by oxidation of unsaturated compounds with ozone in ozone treatment are contained, the total convent of the dissolved ozone and ozonization intermediate is from 15 to 200 ppm in terms of ozone. In this content, the content of an ozonization intermediate is from 5 to 200 ppm, and the content of an ozonization intermediate can be changed by distillation conditions of the primary-purification. Namely, it varies depending on the amount of unsaturated compounds removed and the ozone treatment method.

A purification method in which crude acetic anhydride is distilled before subjected to ozone treatment is described above as the method for obtaining acetic anhydride of the present invention, however, the method is not restricted to this purification method, and acetic anhydride of the present invention may be obtained by any purification method providing the acetic anhydride satisfied the condition that the value of a sulfuric acid coloring test after performing heat treatment at 80 to 120° C. for 5 hours or more is 10 APHA or less.

In acetic anhydride of the present invention, generation of novel unsaturated compounds is suppressed even by for example heating and the like, consequently, hue does not deteriorate, and the quality thereof is maintained stably. Therefore, acetic anhydride of the present invention can be applied, in addition to use as acetic anhydride used in the above-mentioned PTMG product, also to uses such as a raw material of cellulose acetate, pharmaceuticals, agricultural chemicals (acephate, etc.), dyes, face washing agents, sweeteners (aspartame, etc.), plasticizers (tributyl citrate, etc.), polymer field (polyacetal, liquid crystal polymer, etc.) and the like, and polyacetal and liquid polymer are particularly suitable. Acetic acid of the present invention is not restricted to them and can be applied to any use, for example, can be used in use requiring treatment of adding heat. Acetic acid of the present invention has a value of a sulfuric acid coloring test after performing the heat treatment at 80 to 120° C. for 5 hours or more, preferably 6 hours or more, further preferably 10 hours or more, further 60 hours or more is 10 APHA or less. The sulfuric acid coloring test is effected by adding 0.3 ml of sulfuric acid to 30 ml of a sample, and after 5 minutes at 25° C., expressing the colored condition in terms of APHA. That having lower APHA value expressing colored condition in the sulfuric acid coloring test is acetic acid having excellent quality.

EXAMPLES

The following examples, reference examples and comparative examples will illustrate the present invention, but do not limit the scope of the present invention.

First, as the product acetic anhydride used in production of PTMG, various product acetic anhydrides were obtained by various purification methods as described in the following experiments No. 1 to No. 3.

[Experiment No. 1 (purification method: distillation+ozone treatment)]

A ketene obtained by thermal decomposition of acetic acid through a ketene furnace was absorbed in acetic acid to obtain crud acetic anhydride, this crude acetic anhydride was passed sequentially through a lower boiling point fraction-removing column and a higher boiling point faction-removing column each operation pressure of which was maintained at normal pressure, to conduct primary-purification treatment. Then, ozone treatment was conducted using an experimental apparatus shown in FIG. 1 on the crude acetic anhydride subjected to this primary purification treatment.

In FIG. 1, 1 represents an ozone generator, and 2 represents a packed column. Ozone was generated from the ozone generator 1 using air as a raw material, and ozonized air (mixed gas of ozone and air) discharged from this ozone generator 1 was introduced to the packed column 2 equipped with a raschig ring of internal diameter 5 mm×height 5 mm through the lower part thereof. In this operation, the ozonized air amount was 42 NL/H, the ozone concentration was 19.0 g/Nm$^3$, and the ozone inflow amount was 38.3 mol/H. On the other hand, the crude acetic anhydride subjected to the primary-purification treatment by distillation as described above was charged into the packed column 2 through the upper part, and allowed to contact countercurrent with ozone, to effect ozone treatment. The product acetic anhydride subjected to the ozone treatment was extracted through the lower part of the packed column 2, and recovered. In this procedure, the charge flow amount of acetic anhydride was 6006 g/H, and the ozone use ratio was 134.3 g-O$_3$/T. The diketene concentration of the crude acetic anhydride was 76 ppm. The diketene concentration of the resulted product acetic anhydride was the detection limit (2 ppm) or less. Analysis of the diketene concentration was conducted by gas chromatography (column; DB-1 (capillary column), detector; FID).

The diketene concentration in the product acetic anhydride was measured by the same manner as in the above-mentioned experiment except that the charge flow amount of the crude acetic anhydride subjected to the primary-purification treatment was 6279 g/H, the ozone inflow amount was 27.4 mol/H, and the ozone use ratio in this was 93.6 g-O$_3$/T. The diketene concentration was the detection limit (2 ppm) or less.

As shown in the results of Experiment No. 1, when the ozone used ratio is over 90 g-O$_3$/T, the diketene concentration was the detection limit (2 ppm) or less.

[Experiment No. 2 (purification method: ozone treatment+distillation)]

In the apparatus shown in FIG. 1, ozonized air having an ozone concentration of 20 g/Nm$^3$ was introduced into the packed column 2 through the lower part at a rate of 150 NL/H. On the other hand, the crude acetic anhydride was charged into the packed column 2 through the upper part at 6000 g/H, and allowed to contact countercurrent with ozone, to effect ozone treatment. Acetic anhydride after the ozone treatment extracted through the lower part of the packed column 2 was introduced continuously to 13th-stage from the top of a distillation column (internal diameter 40 mm, made of glass) having 30 stages at 400 gH, and the column was operated at a reflux ratio of 200 and a top pressure of 1 atm. The condensed lower boiling point fraction was extracted from the condensed liquid at the top at a ratio of 2 g/H, and the purified acetic anhydride was extracted from 27th-stage by vapor side cut at a ratio of 392 g/H, continuously. Further, acetic anhydride containing higher boiling substances was extracted continuously from the bottom at a ratio of 6 g/H. The diketene concentration of crude acetic anhydride extracted from 27th-stage was 7 ppm.

As apparent from Experiment No. 1 and Experiment No. 2 and the like, the diketene concentration in the product acetic anhydride when purification treatment was conducted according to a purification method in which ozone treatment is conducted previously, then, distillation treatment is conducted through the lower boiling point fraction-removing column and the higher boiling point fraction-removing column was at least about 5 ppm. Therefore, when a purification method in which distillation treatment is conducted previously, then, ozone treatment is conducted is used, the content of diketenes is the detection limit or less, and a product acetic anhydride having more high quality can be produced.

[Experiment No. 3 (purification method: distillation only)]

Crude acetic anhydride was introduced continuously to 13th-stage from the top of a distillation column (internal diameter 40 mm, made of glass) having 30 stages sieve trays at 400 gH, and the column was operated at a reflux ratio of 200 and a top pressure of 1 atm. The condensed lower boiling point fraction was extracted from the condensed liquid at the top at a ratio of 2 g/H, and the purified acetic anhydride was extracted from 27th-stage by vapor side cut at a ratio of 392 g/H, continuously. Further, acetic anhydride containing higher boiling substances was extracted continuously from the bottom at a ratio of 6 g/H. The diketene concentration of crude acetic anhydride extracted from 27th-stage was 98 ppm.

Next, an example of producing PTMG using the product acetic anhydride obtained in the above-mentioned Experiment No. 1, an example of producing PTMG using the product acetic anhydride of Experiment No. 2 and an example of producing PTMG using the product acetic anhydride of Experiment No. 3 are explained as Example 1, Example 2 and Comparative Example 1, respectively.

Example 1

2000 parts by weight of THF, and 332 parts by weight of the acetic anhydride having a diketene concentration of the detection limit or less obtained in Experiment 1 were reacted at 40° C. for 8 hours in a reactor equipped with a stirrer using as a catalyst 100 parts by weight of a zirconia. silica powder baked at 800° C. After completion of the reaction, the catalyst was filtrated, and unreacted THF and acetic anhydride were distilled off from colorless polymerization liquid under reduced pressure, to obtain PTMGA. Then a mixture of 1000 parts by weight of this PTMGAC, 1000 parts by weight of methanol and 1 part by weight of calcium hydroxide was charged into a reactor equipped with a distillation column having a theoretical stage number of 20, and heated under boiling for 6 hours while stirring to effect ester exchange while distilling off an azeotropic mixture of methanol/methyl acetate from the top of the distillation column.

The reaction solution was cooled, then, filtrated through a pressure filtration apparatus equipped with a 1 μm filter, to remove calcium hydroxide, giving 1910 parts by weight of a colorless and transparent filtrate. This filtrate was passed through an adsorption column of 30° C. filled with a strong acidic cation exchange resin of sulfonic acid type, to remove dissolved calcium hydroxide.

The treated liquid was deprived of most of methanol under normal pressure in an evaporator, then, treated continuously in a thin layer evaporator operated at a heat medium temperature of 250° C. under reduced pressure of 10 torr, to obtain 870 parts by weight of PTMG containing substantially no methanol. The hue evaluation results of the resulted PTMG are shown in Table 1.

Example 2

PTMG was produced in the same manner as in Example 1 except that that having a diketene concentration of 7 ppm obtained in Experiment No. 2 was used as the acetic anhydride used in ring-opening-polymerizing THF. The hue evaluation results of the resulted PTMG are shown in Table 1.

Comparative Example 1

PTMG was produced in the same manner as in Example 1 except that that having a diketene concentration of 98 ppm obtained in Experiment No. 3 was used as the acetic anhydride used in ring-opening-polymerizing THF. The hue evaluation results of the resulted PTMG are shown in Table 1.

TABLE 1

| | Diketene concentration of acetic anhydride used | Result hue evaluation |
|---|---|---|
| Example 1 | ND | ⊚ |
| Example 2 | 7 ppm | ○ |
| Comparative Example 1 | 98 ppm | x |

⊚: colorless and transparent, ○: somewhat colored, x: colored

As shown in this table, when acetic anhydride used in ring-opening-polymerizing THF has a diketene concentration of 10 ppm or less, hue increases significantly as compared with PTMG produced by using acetic anhydride having a diketene concentration higher than this concentration, further, when acetic anhydride containing little diketene having a diketene concentration of the detection limit or less is used, colorless and transparent PTMG of high quality is obtained.

Example 3

A ketene obtained by thermal decomposition of acetic acid through a ketene furnace was absorbed in acetic acid to obtain crud acetic anhydride, this crude acetic anhydride was passed sequentially through a lower boiling point fraction-removing column and a higher boiling point faction-removing column each operation pressure of which was maintained at normal pressure, to conduct primary-purification treatment. Then, ozone treatment was conducted using an experimental apparatus shown in FIG. 1 on the crude acetic anhydride subjected to this primary purification treatment.

Ozone was generated from the ozone generator 1 using air as a raw material, and ozonized air (mixed gas of ozone and air) discharged from this ozone generator 1 was introduced to the packed column 2 equipped with a raschig ring of external diameter 5 mm×height 5 mm through the lower part thereof. In this operation, the ozonized air amount was 42 NL/H, the ozone concentration was 19.0 g/Nm$^3$, and the ozone inflow amount was 16.6 mol/H.

On the other hand, the crude acetic anhydride subjected to the primary-purification treatment by distillation as described above was charged into the packed column 2 through the upper part, and allowed to contact countercurrent with ozone, to effect ozone treatment. The product acetic anhydride subjected to the ozone treatment was extracted through the lower part of the packed column 2, and recovered. In this procedure, the charge flow amount of acetic anhydride was 6006 g/H, and the ozone use ratio was 133 g-O$_3$/T.

Thus obtained crude acetic anhydride had a purity of 99.5%, the total content of dissolved ozone and the ozonization intermediate was 92 ppm in terms of ozone, and of this content, the content of the ozonization intermediate was 69 ppm.

Measurement of the total content of dissolved ozone and the ozonization intermediate was conducted by the following procedure according to KI method.

① 100 g of pure water is added to 10 g of a sample, and they are hydrolyzed and left for 20 minutes.
② 30 cc of 0.2 N KI aqueous solution is added to 10 cc of a sample.
③ 5 cc of a 2N sulfuric acid aqueous solution is added.
④ cooled in a refrigerator (5° C.) for 20 minutes or more.
⑤ titration with sodium thiosulfate (indicator starch aqueous solution).

By such measurement, the total content of dissolved ozone and ozonization intermediate was calculated in terms of ozone.

On the other hand, measurement of the content of dissolved ozone in acetic anhydride containing dissolved ozone and an ozonization intermediate in admixture was conducted by adding a given amount of diketene, and measuring the remaining amount of this diketene by gas chromatograph analysis (hereinafter, referred to as DK method). Namely, when a diketene is added, this is oxidized with dissolved ozone, and a diketene of the same amount as dissolve ozone disappears. Therefore, reduction amount obtained by subtracting the measured diketene remaining amount from the addition amount of the diketene, namely, the amount of the diketene disappeared in the reaction with dissolve ozone can be calculated, to be used as the amount of dissolved ozone. Further, the value obtained by subtracting the content of dissolved ozone obtained by DK method, from the total content of dissolved ozone and an ozonization intermediate obtained by the above-mentioned KI method, was used as the content of an ozonization intermediate.

Measurement of the concentration of diketenes as unsaturated compounds was conducted together. This concentration was 76 ppm in crude acetic anhydride, and the diketene concentration in the resulted product acetic anhydride was detection limit (2 ppm) or less.

The crude acetic anhydride obtained as described above was subjected to the sulfuric acid coloring test as described below. Namely, 0.3 ml of sulfuric acid was added to 30 ml of a sample, and after 5 minutes at 25° C., colored condition thereof was expressed by APHA.

Next, the crude acetic anhydride obtained as described above was subjected to heat treatment at 110° C. for 6 hours, then, to the sulfuric acid coloring test in the same manner as described above. Further, the sulfuric acid coloring test of the purified acetic anhydride after the heat treatment was conducted for 10 hours, 30 hours and 60 hours.

The measured values of the above-mentioned acetic anhydrides are summarized in Table 1.

Example 4

Acetic anhydride was produced in the same manner as in Example 3 except that the amount of the ozonized air introduced in the packed column 2 in ozone treatment was 120 NL/H in the process of producing acetic anhydride in Example 3.

The resulted crude acetic anhydride had a purity of 99.5%, the total content of dissolved ozone and the ozonization intermediate was 124 ppm in terms of ozone, and of this content, the content of the ozonization intermediate was 112 ppm. The diketene concentration was detection limit (2 ppm) or less.

The crude acetic anhydride obtained as described above, and that obtained by heating this at 110° C. for 6 hours were subjected to the sulfuric acid coloring test in the same manner as in Example 3.

The measured values of the acetic anhydrides are summarized in Table 1.

Reference Example 1

In the same manner as in Example 3, a ketene obtained by thermal decomposition of acetic acid through a ketene furnace was absorbed in acetic acid to obtain crud acetic anhydride, this crude acetic anhydride was first subjected to ozone treatment, then, to distillation to obtain a product acetic anhydride. In the ozone treatment, in the apparatus shown in FIG. 1, ozonized air having an ozone concentration of 20 g/Nm$^3$ was introduced into the packed column 2 through the lower part at a rate of 150 NL/H. On the other hand, the crude acetic anhydride was charged into the packed column 2 through the upper part at 6000 g/H, and allowed to contact countercurrent with ozone, to effect ozone treatment.

Then, acetic anhydride after the ozone treatment extracted through the lower part of the packed column 2 was introduced continuously to 14th-stage from the top of a distillation column (internal diameter 40 mm, made of glass) having 30 stages at 500 gH, and the column was operated at a reflux ratio of 5 and a top pressure of 1 atm. The condensed lower boiling point fraction was extracted from the condensed liquid at the top at a ratio of 100 g/H, and the purified acetic anhydride was extracted from 26th-stage by vapor side cut at a ratio of 396 g/H, continuously. Further, acetic anhydride containing higher boiling substances was extracted continuously from the bottom at a ratio of 6 g/H.

The resulted crude acetic anhydride had a purity of 99.6%, the total content of dissolved ozone and the ozonization intermediate was 33 ppm in terms of ozone, and of this content, the content of the dissolved ozone was the detection limit (10 ppm) or less. The diketene concentration was 8 ppm.

The crude acetic anhydride obtained as described above, and that obtained by heating this at 110° C. for 6 hours were subjected to the sulfuric acid coloring test in the same manner as in Example 3.

The measured values of the acetic anhydrides are summarized in Table 2.

Reference Example 2

Crude acetic anhydride obtained in the same manner as described above was introduced continuously to 14th-stage from the top of a distillation column (internal diameter 40 mm, made of glass) having 30 stages at 500 gH, and the column was operated at a reflux ratio of 5 and a top pressure of 100 Torr. The condensed lower boiling point fraction was extracted from the condensed liquid at the top at a ratio of 100 g/H, and the purified acetic anhydride was extracted from 26th-stage by vapor side cut at a ratio of 394 g/H, continuously.

The resulted crude acetic anhydride had a purity of 99.6%, the total content of dissolved ozone and the ozonization intermediate was 60 ppm in terms of ozone, and of this content, the content of the dissolved ozone was the detection limit (10 ppm) or less. The diketene concentration was 3 ppm.

The crude acetic anhydride obtained as described above, and that obtained by heating this at 110° C. for 6 hours were subjected to the sulfuric acid coloring test in the same manner as in Example 3.

The measured values of the acetic anhydrides are summarized in Table 2.

Reference Example 3

In the same manner as in Example 3, a ketene obtained by thermal decomposition of acetic acid through a ketene furnace was absorbed in acetic acid to obtain crud acetic anhydride, this crude acetic anhydride was subjected to ozone treatment. In the ozone treatment, in the apparatus shown in FIG. 1, ozonized air having an ozone concentration of 21 g/Nm$^3$ was allowed to contact for 1 hour while bubbling at 75 NL/H, to conduct treatment. The resulted crude acetic anhydride had a purity of 85.5%, the total content of dissolved ozone and the ozonization intermediate was 150 ppm in terms of ozone, and of this content, the content of the dissolved ozone was 27 ppm, and the diketene concentration was 123 ppm.

The crude acetic anhydride obtained as described above, and that obtained by heating this at 110° C. for 6 hours were subjected to the sulfuric acid coloring test in the same manner as in Example 3.

The measured values of the acetic anhydrides are summarized in Table 2.

TABLE 2

|  | Example 3 | Example 4 | Reference Example 1 | Reference Example 2 | Reference Example 3 |
|---|---|---|---|---|---|
| Purity (%) | 99.5 | 99.5 | 99.6 | 99.6 | 85.5 |
| Amount of dissolved ozone + ozonized intermediate (ppm) | 92 | 124 | 33 | 60 | 150 |
| Amount of dissolved ozone (ppm) | 23 | 12 | Not detected | Not detected | 27 |
| Amount of ozonized intermediate (ppm) | 69 | 112 | 33 | 60 | 123 |
| Diketene concentration (ppm) | Not detected | Not detected | 8 | 3 | — |
| Appearance | No coloring | No coloring | No coloring | No coloring | No coloring |
| Result of sulfuric acid coloring test (APHA) After heat treatment (110° C., 6 hours) | 10 or less | 10 or less | 10 or less | 10 or less | 10 or less |
| Appearance | No coloring | No coloring | Coloring recognized (pale yellow) | Coloring recognized (pale yellow) | Coloring recognized (yellow to brown) |
| Result of sulfuric acid coloring test (APHA) | 10 or less | 10 or less | 20 | 20 | 60 |
| Sulfuric acid coloring test (APHA) After 10 hours | 10 or less | 10 or less | 20 | 20 | — |
| Sulfuric acid coloring test (APHA) After 30 hours | 10 or less | 10 or less | 20 | 20 | — |
| Sulfuric acid coloring test (APHA) After 60 hours | 10 or less | 10 or less | 30 | 30 | — |

As apparent from Table 2, the crude acetic acids of the present invention (Examples 3, 4) had no coloring after the heat treatment, and the values of APHA of the sulfuric acid coloring test (test time 5 minutes) after the heat treatment were low. Further, even when the test time was elongated to 10 hours, 30 hours and 60 hours, the value of APHA was low. However, the acetic anhydrides of Reference Examples 1 to 3 were colored after the heat treatment, and the values of APHA of the sulfuric acid coloring test (test time 5 minutes) after the heat treatment were low. Further, in the crude acetic acids of Reference Examples 1, 2, when the test time of the sulfuric acid coloring test was 60 hours, further higher value of APHA than in the case of a test time of 5 minutes was shown.

According to the present invention, crude acetic anhydride having smaller diketene content can be obtained. By using acetic anhydride having such small diketene concentration, products such as PTMG and the like having excellent hue can be produced.

Further, according to the present invention, purified acetic anhydride which causes not problem in quality such as coloring and the like by heating and the like can be provided. Such acetic anhydride of the present invention has high purity and has stable qualities such as hue and the like, therefore, it can be used widely for producing polyacetal and liquid crystal polymer, and as an acetylation agent for an organic chemicals, and the like.

What is claimed is:

1. A method of purifying crude acetic anhydride wherein treatment with an ozone-containing gas is conducted after distilling acetic anhydride containing diketenes.

2. A method of purifying crude acetic anhydride as recited in claim 1 wherein said purified crude acetic anhydride has a diketene concentration below 2 ppm.

3. A method of purifying crude acetic anhydride as recited in claim 1 wherein said purified crude acetic anhydride, after performing a heat treatment of between 80 and 120 degrees Celsius for at least 5 hours, has a hue value of 10 APHA units or less subsequent to a sulfuric acid coloring test.

4. A method of purifying crude acetic anhydride as recited in claim 3 wherein said purified crude acetic anhydride has a diketene concentration below 2 ppm.

5. A method of producing polyoxytetramethylene glycol by ring-opening polymerization of tetrahydrofuran in the presence of acetic anhydride and an acid catalyst, comprising:

purifying said acetic anhydride by treatment with an ozone-containing gas after distilling crude acetic anhydride containing diketenes;

conducting the ring-opening-polymerization with said purified acetic anhydride and said acid catalyst.

* * * * *